United States Patent [19]

Swedberg

[11] Patent Number: 5,114,768

[45] Date of Patent: * May 19, 1992

[54] SURFACES WITH REDUCED PROTEIN INTERACTIONS

[75] Inventor: Sally A. Swedberg, Santa Cruz, Calif.

[73] Assignee: Hewlett-Packard Company, Palo Alto, Calif.

[*] Notice: The portion of the term of this patent subsequent to Jun. 5, 2007 has been disclaimed.

[21] Appl. No.: 507,937

[22] Filed: Apr. 11, 1990

Related U.S. Application Data

[63] Continuation-in-part of Ser. No. 7,234,456, Aug. 19, 1988, Pat. No. 4,931,328.

[30] Foreign Application Priority Data

Jun. 2, 1988 [WO] PCT Int'l Appl. ... PCT/US88/01877

[51] Int. Cl.$^5$ ...................... B29D 22/00; C25D 13/00
[52] U.S. Cl. ................................. 428/36.91; 428/420; 204/180.1; 204/182.8; 204/299 R; 128/760; 128/763; 604/403

[58] Field of Search ............. 204/299 R, 180.1, 182.8; 428/34.7, 36.91, 426, 420; 128/760, 763; 604/403

[56] References Cited

U.S. PATENT DOCUMENTS 4,680,201  7/1987  Hjerten ................................. 427/230
4,690,749  9/1987  Van Alstine et al. .............. 428/403

*Primary Examiner*—James J. Seidleck
*Assistant Examiner*—J. Weddington

[57] ABSTRACT

A solid surface that is exposed to protein solutes in use, such as medical implants or capillary tubes useful in capillary zone electrophoresis, is defined by or carries a polymer. An interfacial layer is covalently bound to the polymer and functions to reduce interactions between the surface and protein solutes. The interfacial layer includes either a hydratable amphoteric phase or a plurality of halogen atoms bound in the interfacial layer through at least one heteroatom.

22 Claims, No Drawings

SURFACES WITH REDUCED PROTEIN INTERACTIONS

This is a continuation-in-part of pending U.S. application Ser. No. 234,456, filed Aug. 19, 1988 now U.S. Pat. No. 4,931,328, issued Jun. 5, 1990, and pending application PCT PA PC US 88 01877, filed Jun. 2, 1988 now issued in the United States U.S. Pat. No. 5,006,313 issued Apr. 9 1991, both of common assignment herewith.

FIELD OF THE INVENTION

The present invention generally relates to solid surfaces exposed to protein solutes, and particularly to capillaries used in electrophoretic separations by capillary zone electrophoresis.

BACKGROUND OF THE INVENTION

Electrophoresis is a well-known technique for the separation of charged species by utilizing their differences in rate of migration under the influence of an electrical field. The prototype of all modern electrophoretic methods is free, or moving-boundary, electrophoresis. The mobility $\mu$ in square centimeters per volt-second of a molecule in an electric field is given by the ratio of the velocity of migration v, in centimeters per second, to electric field strength E, in volts per centimeter: $\mu = v/E$. For small ions, such as chloride, $\mu$ is between 4 and $9 \times 10^{-4}$ cm$^2$ v$^{-1}$ s$^{-1}$ (25° C.); for proteins, it is about 0.1 to $1.0 \times 10^{-4}$ cm$^2$ v$^{-1}$ s$^{-1}$. Protein thus migrates much more slowly in an electrical field than small ions simply because they have a much smaller ratio of charge to mass.

Free electrophoresis has been largely supplanted by various forms of zone electrophoresis in which the aqueous protein solution is immobilized in a solid matrix that provides mechanical rigidity and reduces convection and vibration disturbances. Matrix material that is porous also allows for sieving. This form of zone electrophoresis can separate a protein mixture on the basis of both electric charge and molecular size, thereby providing high resolution.

Capillary zone electrophoresis ("CZE") in small bore capillaries was first demonstrated by Jorgenson and Lukacs, and has proven useful as an efficient method for the separation of certain small solutes *J. Chromatog.*, 218 (1981), page 209; Anal. Chem., 53 (1981) page 1298. Attractive factors for CZE include the small sample sizes, little or no sample pretreatment, high resolution, automation, and the potential for quantification and recovery of biologically active samples. For example, U.S. Pat. No. 4,675,300, inventors Zare et al., issued Jun. 23, 1987 describes theories and equipment for electrokinetic separation processes employing a laser-excited fluorescence detector. The system described by Zare et al. includes a fused silica capillary with a 75$\mu$ inner diameter.

Unfortunately, one of the single greatest disadvantages of capillary zone electrophoresis lies when attempts are made to separate macromolecules such as proteins. Separations of macromolecules by CZE leads to untoward interactions of the biopolymers with the silica capillary wall.

Jorgenson and Lukacs had noted that separation of model proteins, such as cytochrome, lysozyme and ribonuclease A, in untreated fused silica capillaries with a phosphate buffer at pH 7 was accompanied by strong tailing, and suggested this might be caused by Coulombic interactions of the positively charged proteins and the negatively charged capillary wall. Jorgensen et al., *Science*, 222 (1983) pages 266-272. The authors reported investigating Teflon capillaries but found these to also exhibit significant adsorptivity toward proteins. They attempted to deactivate the surface of fused silica with groups such as trimethyl silane, octadecylsilane, amino-propylsilane, and cross-linked methyl cellulose, which apparently did not succeed. They then turned to bonding glycol-containing groups to the surface.

Lauer and McManigill, *Analytical Chemistry*, 58 (1986), page 166, have reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge. However, disadvantages of this approach are that silica begins to dissolve above pH 7, which shortens column life and degrades performance, only proteins with pI's less than the buffer pH can be analyzed, which drastically reduces the range of useful analysis, and interactions which are not Coulombic may still occur even with proteins bearing a net negative charge due to the complexity of protein composition and structure.

Another approach to the problem of biopolymer, or protein, interactions has been to increase ionic strength. It has been demonstrated that this concept works in principle, but heating is also increased as ionic strength is increased. This heating tends to degrade the efficiency of separation.

Yet another approach to the problem of undesirable protein interactions with the capillary wall has been to coat the electrophoresis tube with a monomolecular layer of non-crosslinked polymer. Thus, U.S. Pat. No. 4,680,201, inventor Hjerten, issued Jul. 14, 1987 describes a method for preparing a thin-wall, narrow-bore capillary tube for electrophoretic separations by use of a bifunctional compound in which one group reacts specifically with the glass wall and the other with a monomer taking part in a polymerization process. This free-radical procedure results in a polymer coating, such as polyacrylamide coating, and is suggested for use in coating other polymers, such as poly(vinyl alcohol) and poly(vinylpyrrolidone). However, this method and capillary tube treatment tends to destroy the electroosmotic flow, and efficiencies are still rather low. These rather low efficiencies suggest that undesirable protein-wall interactions are still occurring.

U.S. Pat. No. 4,690,749, issued Sep. 1, 1987, Van Alstine et al., discloses activating a glass surface with aminosilanes to alter reactive surface groups from silanols to amines. Van Alstine et al. teach use of neutral polymers, such as polyethylene glycol or dextran polymer, to be covalently bound to the electrophoretic surface. The data presented by Van Alstine et al. show their treatment reduces electroosmotic flow, which is consistent with their view that electroosmotic flow is not desirable.

SUMMARY OF THE INVENTION

It is an object of the present invention to provide capillary tubes that are useful for electrophoretic separations of solutes including macromolecules, with interactions between the solutes and the bore being reduced considerably, and with high efficiencies.

It is another object of the present invention to provide capillary tubes permitting electroosmotic flow control, such as control of flow magnitude and/or flow direction.

Further objects and advantages of the invention will become apparent to those skilled in the art upon examination of the specification and appended claims, as well as in practice of the present invention.

In one aspect of the present invention, an article of manufacture is provided that is exposed to protein solutes when used. Particularly preferred articles of the invention are formed as capillary tubes and are useful in capillary zone electrophoresis to separate protein solutes. The inventive articles have a solid surface that is defined by or carries a polymer. An interfacial layer is covalently bound to the polymer. The interfacial layer functions to reduce interactions between the surface and protein solutes. The interfacial layer includes either a hydratable amphoteric phase or a plurality of halogen atoms that are bound through at least one heteroatom.

DETAILED DESCRIPTION OF THE PREFERRED EMBODIMENTS

The present invention provides a solid surface formed of a wide range of materials (beyond use of only silica), which surface is modified so as to have reduced interactions with protein solutes. For example, implants to repair or replace body parts are exposed to protein solutes and physi-sorb proteins unless modified. One particularly preferred application is for small bore capillary tubes, such as tubes useful in capillary zone electrophoresis. These tubes are usually less than 500μ, more typically about 20μ to about 200μ, in internal diameter. Other applications include medical uses, such as heart-lung machines where surfaces are exposed to protein solutes. For convenience, reference will hereinafter be to a small bore (less than about 500 microns) capillary tube with the bore having been modified in accordance with the invention.

The modification is whereby a reduced interaction phase extends along the bore, or inside wall, as an interfacial layer between the inside wall of the capillary and the protein solutions when in use. The reduced interaction phase is effective to reduce interactions between protein solutes and the bore, preferably while permitting reasonably high electroosmotic flow and resulting in excellent efficiencies. This interfacial layer is preferably about four to about six molecular layers thick, so that electroosmotic flow is reasonably high in use for capillary zone electrophoresis; however, fewer molecular layers (so long as at least one) or greater molecular layers are possible, and may be desirable for particular applications. When bulk molecular layers are carried on the surface, then the electroosmotic flow tends to substantially decrease, which is normally not desired in a system with a single detector with species which migrate towards two electrodes.

As described in my application Ser. No. 234,456, filed Aug. 19, 1988 now U.S. Pat. No. 4,931,328, issued Jun. 5, 1990, when the capillary bore, or inner wall surface to be modified is silica based, it is first hydrated and then reacted with an organo- or chloro-silane having two functional end groups. I have discovered that a wider range of materials, in addition to silica, can be modified so as to have reduced interactions with protein solutes. These additional materials are generally polymers, which can form the capillary tubing itself or can be coated on or bonded within a silica capillary wall. That is, when the polymers do not themselves form, or define, the capillary tube, then they are carried by the inner wall of the tube and the interfacial layer is further coated onto the polymer.

By expanding the scope of useful capillary materials beyond silica one gains an advantage of practicing at wider ranges than the pH range of from about 2-7 in which use of silica restricts one. That is, by the polymer modifications hereinafter described in more detail, one can operate in pH ranges from about 2-10 and, in many instances, at even higher pH ranges such as on the order of about 11-12.

In selecting an appropriate polymer for use in practice of the present invention, one considers the following criteria and looks for: a high resistivity to electric fields, a material that is nonporous and permits some manipulations during separations, a material that is electrically non-conductive, is relatively stable in the high salt, aqueous media in which separations are performed and, preferably, where the material provides a relatively wide range of transmission in UV and visible wavelengths for on-column detections (although post-column detection is possible).

Among the polymeric materials that meet these criteria are nylon, styrene or phenyl silicones, acrylics, polyurethanes, polycarbonates, polyesters, silicon alkoxy elastomers, and fluorocarbons. Although silica is a very high energy surface and the polymeric materials can provide a relatively lower energy surface, the polymeric surfaces still need to be modified to reduce protein interactions along the surface. These polymeric surfaces are modified, in accordance with the invention, to precursor surfaces. The precursor surfaces are then further preferably treated so as to add the interfacial layer modified in one of several different ways. The several different ways represent different embodiments of the invention.

The polymers used must provide multi-point attachments with the moieties that will form the preferred embodiments in the further modification of precursor surfaces. Two such embodiments are where a hydratable amphoteric phase is formed or where covalently bound halogen moieties are attached. Both the amphoteric phase and the halogen containing phase are derived from precursor surfaces. The precursor surfaces are polymeric surfaces that have been modified to include reactive nitrogen nucleophiles, oxygen nucleophiles or carbon electrophiles. Illustrative modifications for a variety of suitable initial polymeric surfaces will now be described.

The polymeric surfaces are modified, or prepared to receive the interfacial layer by activating certain functional groups. These functional groups typically are oxygen or nitrogen nucleophiles and can also be a carbon electrophile.

The multi-point attachments of the polymers can be accomplished through various functional groups. Illustrative functional groups include hydroxyl (as an oxygen nucleophile), carboxyl (as a carbon electrophile) and amino (as nitrogen nucleophile). Specific examples of polymers with these illustrative functional groups are hydroxyl alkyl methacrylates (hydroxy methyl methacrylate and hydroxy ethyl methacrylate) and hydroxy silicone rubbers. Examples of carboxyl containing polymers are nylons and esters such as methylmethacrylate. Examples of polymers with amino functional groups are nylons and styrenes.

Where, for example, one desires to use styrene, then the multi-point attachments through which the interfacial layer will be bonded will normally be amine groups. One useful technique for preparing the functional amine groups is by perfusing the styrene surface with 47% nitric acid in sulfuric acid at 0° C. for 20 minutes at a flow rate of 1-2 column volumes per minute. The capillary is flushed with water at 1-2 column volumes per minute for $\frac{1}{2}$-1 hour. Reduction can the be accomplished such as with 6% $Na_2S_2O_4$ in 2.0M sodium hydroxide at 1-2 column volumes per minute.

If one chooses nylon as the polymeric material, then an amine carboxyl group can be used as the functionality through which the interfacial layer will be attached. The nylon surface may be prepared by perfusing 4N hydrochloric acid through the capillary at a rate of 1-2 column volumes per minute for 30 minutes-1 hour at 35.C. The excess hydrochloric acid is flushed out of the tubing with deionized water at 1-2 column volumes per minute for $\frac{1}{2}$-1 hour. This provides hydrolytic cleavage. For non hydrolytic cleavage, the nylon surface may be activated by perfusing the capillary at 1-2 column volumes per minutes for 10-15 hours with N, N-dimethylaminopropylamine at 70° C. The excess free agent is flushed with ethanol and then water.

Where one wishes to use esters such as methyl methacrylate, then an activated carboxyl can be obtained by perfusing the capillary at a rate of 1-2 column volumes per minute with 95% hydrazine at 70° C. for 8-10 hours. The excess is flushed for 1-2 column volumes per minute for 30 minutes-1 hour, first with ethanol and then with water.

A hydroxy alkyl methacrylate can be coupled directly through an oxygen nucleophile.

Hydroxyl containing surfaces can be activated in a large number of ways. Generally, all such functional group activations of polymer surfaces are known to persons skilled in the art. Once activated, then the interfacial layer is formed.

When the capillaries are prepared and ready for reaction with the species that will form the desired interfacial layers, then one can proceed with either embodiment of the invention. For example, solutions of desired hydratable amphoteric compounds can be prepared as 0.2mM concentrations in 0.1M phosphate buffer, pH 7.0. The ends of the columns are then sealed, and the columns allowed to sit for a minimum of about 2 hours at 4° C. in order to form a reaction product of the protein, peptide or synthetic ampholyte with the activated oxygen or nitrogen nucleophile of the column. The excess, unreacted amphoteric compounds can then be washed away at flow rates of 1-2 mL/minute for approximately 2-3 hours with the appropriate starting buffer.

Alternatively, where the halogen containing embodiment is desired, the prepared capillaries can be reacted with, for example, a 0.2M solution of an acyl chloride (e.g. pentafluorobenzoyl chloride) by pumping through the column followed by washing with toluene, methanol and then water.

Two particularly preferred embodiments of the interfacial layer will now be described. One embodiment will sometimes be called "first embodiment" capillary tubes and is where the interfacial layer includes a hydratable amphoteric phase. Another, or "second embodiment" is where the interfacial layer includes a terminal moiety that is covalently bound through at least one heteroatom.

First embodiment capillary tubes have an interfacial layer that includes a hydratable amphoteric phase, prepared by reacting (that is, covalently bonding, or coupling) a protein, peptide or an ampholyte with the oxygen or nitrogen nucleophiles of the precursor surfaces as previously described. The amino groups (of the nitrogen nucleophile) and the carboxyl or hydroxy groups (of the oxygen nucleophile) are activated to effect the coupling. For example, the amino groups may be activated with glutaraldehyde or carbonyl-diimidazole, and the carboxyl or hydroxy groups with carbonyl-diimidazole. Alternatively, the proteins, peptides and ampholytes themselves may be activated to effect the coupling. Activation for coupling proteins, peptides or ampholytes is well known in the art.

Suitable proteins, peptides and ampholytes for inclusion in the covalently bound interfacial layer have a molecular weight between about 200 daltons to about 58K daltons. That is, molecules in size from dipeptides to macromolecules can be utilized. Ampholytes are particularly preferred because these synthetic molecules are commercially available for particular, narrow pI ranges. As is known, ampholytes may be synthesized by copolymerization of amines and amino acids with epichlorohydrin. By a suitable choice of amines and amino acids, a large part of the buffer capacity can be concentrated into a narrow pH-interval (2-3 pH units). Ampholytes are commercially available from sources such as Pharmacia Fine Chemicals (under the trade name "Pharmalyte") and from Bio-Rad Laboratories (under the trade name "Bio-Lyte").

The amphoteric phase, whether protein, peptide or ampholyte, includes ionizable cationic and ionizable anionic species. The cationic species include amino, guanidinium, imidiazolium and mixtures thereof. Amino species for the cationic species may be obtained from lysine side chains, guanidinium may be obtained from arginine side chains, and imidiazolium from histidine. The anionic species of the amphoteric phase has carboxyl groups from aspartic acid and glutamic acid side chains. The synthetic ampholytes have ionizable cationic species from amino groups, most of which are tertiary, but a few being secondary or primary. The anionic species is provided by carboxyl groups of two kinds: α-amino carboxylic groups and carboxyl groups from polymerized glycylglycine.

The proteins, peptides and ampholytes suitable for forming the amphoteric phase are all highly hydrated under use conditions. This is important for reversibility of interactions (albeit reduced) between the coated surface and the protein solutes. This hydratable amphoteric phase permits control of both electroosmotic flow magnitude and flow direction. Control over the electroosmotic flow magnitude means that efficiencies can be optimized for particular separations. Control over flow direction means that the elution order can be modified, and indeed can be reversed. Reversibility of electroosmotic flow means that a protein that would normally be resolved very slowly can be eluted earlier.

Coatings with the hydratable amphoteric phase embodiment of the invention have resulted in protein separations with efficiencies in the range of 300,000 to about 1,000,000 theoretical plates. These highly efficient separations have been accomplished with very low protein to wall interactions (k'), usually less than 0.02. The electroosmotic flow rates at these very low k' values and high efficiencies are believed to be about optimum for maximum efficiencies.

A second embodiment reduced interaction phase includes a terminal moiety that is covalently bound through at least one heteroatom. The terminal moiety is distal to the surface and covalently bound to the surface by an intermediate linkage including the heteroatom(s). The terminal moiety includes a plurality of halogen atoms, which may be substituents on an aryl group, an alkylaryl group or an alkyl group. Preferably, the terminal moiety is an aryl pentahalo.

Illustrative terminal moieties with halogen atoms substituted on an alkyl group are $CX_3$—$(CX_2)_n$— where n is 0 to about 5 and X is selected from hydrogen and halogen with at least two being halogen.

Illustrative terminal moieties with halogen atoms substituted on an alkyl aryl are

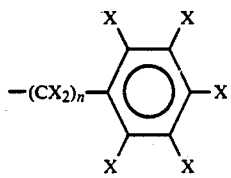

where n is 1 to about 5 and X is selected from hydrogen and halogen with at least two being halogen.

Illustrative terminal moieties substituted on an aryl group are

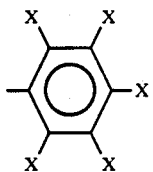

where X is selected from hydrogen and halogen with at least two being halogen.

These terminal moieties are covalently bound to the surface through at least one heteroatom of an intermediate linkage. The heteroatom is nitrogen, preferably of an amino group, oxygen, preferably of a carbonyl group, and may also include sulfur. As will be hereinafter more fully described, several heteroatoms may be present and several are preferred. The heteroatoms increase the hydrophilic character of the reduced interaction phase and, together with the halogen atoms of the terminal moieties, reduce protein interactions with the capillary tube such as caused by van der Waals' forces, hydrogen bonding and point charges.

Particularly preferred linkages including the heteroatoms and being intermediate the surface and the terminal moieties are amides, esters, secondary amines, carbamates, carbonates and dithiols including activated carbonyls.

A modified precursor surface with nitrogen nucleophile, oxygen nucleophile or carbon electrophile is then reacted with the compound having halogen substituents. This halogen compound includes an electrophilic species, when the surface has nitrogen or oxygen nucleophiles, and includes a nucleophilic species, when the surface has carbon electrophiles. Exemplary reagents for the former situation are pentafluorobenzoyl chloride, pentafluorobenzaldehyde, and pentafluorobenzoic acid. An exemplary reagent for the later situation is a 2,3,4,5,6 pentafluoroalkylamine having the structure

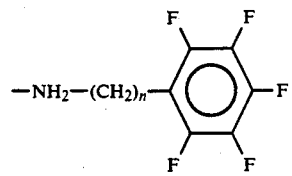

where n is 1 to about 5. When n=1, then the 2,3,4,5,6 pentafluorobenzylamine may be prepared by reduction of the nitrile. However, these electrophilic or nucleophilic halogen compounds may be selected from a wide variety of different compounds. As some further examples are:

2,3,4,5,6-pentafluorobenzhydrol,
Pentafluorobenzonitrile,
2,3,4,5,6-pentafluorobenzyl alcohol,
2,3,4,5,6-pentafluorocinnamic acid,
2,3,4,5,6-pentafluorophenoxyacetic acid,
2,3,4,5,6-pentafluorophenylacetic acid,
DL-1-(pentafluorophenyl) ethanol
Pentafluorophenylhydrazine,
2,2,3,3,3-pentafluoro-1-propanol,
Pentafluoropropionic anhydride,
Pentafluroropyridine,
2,3,4,5,6-pentafluorostyrene,
Pentafluorothiophenol, and
α-Bromo-2,3,4,5,6-pentafluorotoluene.

Rather than reacting the surface modified precursor having nitrogen or oxygen nucleophile or carbon electrophile immediately with the desired halogen compound in preparing the second embodiment surfaces, an intermediary leash step may be performed to attach a spacer arm, or leash. This leash is thus part of the intermediate linkage. An advantage of such a leash step is that additional heteroatoms can be incorporated into the reduced interaction phase.

Appropriate spacer arms for reaction with the nitrogen nucleophile are electrophiles, such as activated carbonyl (e.g., acid halide, anhydride or carbodiimide activated carbonyl or activated ester (such as N-hydroxy succinimide ester), intrinsically reactive carbonyl (e.g., aldehyde), haloalkyl carbon electrophile (e.g., α-haloacetic acid or haloepoxypropanes) and with bisoxiranes. Exemplary activated carboxyl carbonyls are succinyl chloride, succinic anhydride, 1,6-hexanoic acid and carbodiimide such as EDAC(1-ethyl-3-(3-dimethylaminopropyl)-carbodiimide) or dicyclohexyl carbodiimide, and disuccinimidyl tartarate and dithiobis(succinimidyl propionate). Exemplary aldehydes are glutaraldehyde and succinic semialdehyde. Exemplary haloalkyl carbon electrophiles are α-bromoacetic acid and epichlorohydrin. Exemplary bisoxiranes are ethylene glycol diglycidyl ether and 1,4 butanediol biglycidyl ether.

A particular advantage of a dithiol leash (illustrated by the exemplary reagent dithiobis (succinimidyl propionate) is that a reduced interaction phase having such dithiol heteroatoms permits regeneration of the surface by reduction and reformation under mild conditions.

Where the surface has been modified with an oxygen nucleophile (as earlier described), then an intermediary leash step may be performed with spacer arms reacting as carbon electrophiles, such as activated carboxyl carbonyls, α-halo alkyl or epoxide carbon electrophiles. Exemplary activated carboxyl carbonyls are succinyl chloride, succinic anhydride, 1,6-hexanoic acid and carbodiimide (such as EDAC or dicyclohexyl carbodiimide), N-hydroxysuccinimide activated carbonyls (e.g., di-succinimidyl tartrate and dithiobis (succinimidyl propionate)). The latter provides a dithiol leash permitting a regenerable surface as earlier described. Exemplary halo alkyls are α-halocarbonyl (e.g., α-bromoacetic acid) and halo epoxy propanes (e.g., epibromohydrin and epichlorohydrin). Exemplary epoxides are bisoxiranes such as ethylene glycol diglycidyl ether and 1,4-butanediol diglycidyl ether.

Where the surface has been modified with a carbon electrophile, then an intermediary leash step may be used where spacers acting as nucleophiles are selected. Exemplary nucleophilic reagents are diamines, carboxylic acid amines and dithiols.

Although the present invention has been described with reference to specific examples, it should be understood that various modification and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

It is claimed:

1. An article of manufacture being exposed to protein solutes in use comprising:
   a solid surface defined by or carrying a polymer, the polymer selected from the group consisting of nylon, styrene, phenyl silicones, acrylics, polyurethanes, polycarbonates, polyesters, silicon alkoxy elastomers, and fluorocarbons, an interfacial layer covalently bound to the polymer at a plurality of attachment points and effective to reduce interactions between the surface and protein solutes, the interfacial layer including a hydratable amphoteric phase or a plurality of halogen atoms bound in the interfacial layer through at least one heteroatom.

2. The article as in claim 1 formed as a capillary tube with the solid surface being an inner wall of the tube.

3. The article as in claim 2 wherein the amphoteric phase is a reaction product of a protein, a peptide or an ampholyte and an oxygen or nitrogen nucleophile.

4. The article as in claim 3 wherein the amphoteric phase has a determinable isoelectric point and selectively permits electroosmotic flow control.

5. The article as in claim 4 wherein the electroosmotic flow control is selected by solution pH.

6. The article as in claim 5 wherein the amphoteric phase permits control of electroosmotic flow magnitude.

7. The article as in claim 5 wherein the amphoteric phase permits control of electroosmotic flow direction.

8. The article as in claim 2 wherein the amphoteric phase includes ionizable cationic and ionizable anionic species, the cationic species selected from the group consisting of amino, guanidinium, imidazolium and mixtures thereof, the anionic species being carboxyl groups.

9. The article as in claim 8 wherein the amphoteric phase has a buffer capacity within a pH interval of about 2 or 3 pH units.

10. The article as in claim 2 wherein the at least one heteroatom is one or more of nitrogen, oxygen or sulfur.

11. The article as in claim 2 wherein the plurality of halogen atoms are substituents on an aryl group, an alkylaryl group or an alkyl group.

12. The article as in claim 2 wherein the terminal moiety is an aryl pentahalo.

13. The article as in claim 2 wherein the halogen moieties are distal to the inner wall and include the structure

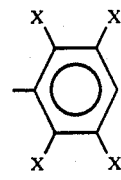

or

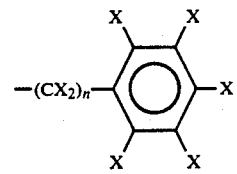

where X is selected from hydrogen and halogen, at least two of X being halogen.

14. The article as in claim 13 wherein the heteroatom is part of an intermediate linkage, the intermediate linkage including at least one of an amide, an ester, a secondary amine, a carbonate, or a carbamate.

15. A capillary tube defining an inner wall, useful for electrophoretic separations of proteins in solution, comprising:
   an interfacial layer covalently bonded to the inner wall and effective to reduce interactions between the inner wall and protein solutes, the inner wall formed by a polymer having a high resistivity to electric fields, being nonporous, electrically nonconductive and relatively stable in the presence of a high salt, aqueous media, the interfacial layer covalently bound to the polymer at a plurality of attachment points, the interfacial layer including a hydratable amphoteric phase or a plurality of halogen atoms bound in the interfacial layer through at least one heteroatom.

16. The capillary tube as in claim 15 wherein the amphoteric phase is a reaction product of a protein, a peptide or an ampholyte and an oxygen or nitrogen nucleophile.

17. The capillary tube as in claim 15 wherein the amphoteric phase includes ionizable cationic and ionizable anionic species, the cationic species selected from the group consisting of amino, guanidinium, imidazolium and mixtures thereof, the anionic species being carboxyl groups.

18. The capillary tube as in claim 15 wherein the at least one heteroatom is one or more of nitrogen, oxygen or sulfur.

19. The capillary tube as in claim 15 wherein the plurality of halogen atoms are substitutents on an aryl group, an alkylaryl group or an alkyl group.

20. The capillary tube as in claim 15 wherein the terminal moiety is an aryl pentahalo.

21. The capillary tube as in claim 15 wherein the halogen moieties are distal to the inner wall and include the structure.

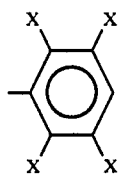
or
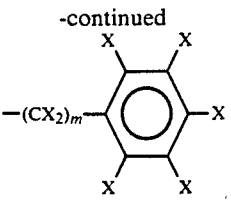
where X is selected from hydrogen and halogen, at least two of X being halogen.
22. The capillary tube as in claim 15 wherein the heteroatom is part of an intermediate linkage, the intermediate linkage including at least one of an amide, an ester, a secondary amine, a carbonate, or a carbamate.
* * * * *